United States Patent [19]

Solomons

[11] Patent Number: 4,971,261
[45] Date of Patent: Nov. 20, 1990

[54] MEDICAL WASTE FRAGMENTATION AND DISPOSAL SYSTEM

[76] Inventor: Charles Solomons, 19 EastLake Dr., Thiells, N.Y. 10984

[21] Appl. No.: 369,841

[22] Filed: Jun. 22, 1989

[51] Int. Cl.$^5$ .............................................. B02C 19/12
[52] U.S. Cl. ..................................... 241/99; 241/100; 241/190; 241/199.12
[58] Field of Search .................. 241/199.12, 101.2, 99, 241/282.1, 282.2, 119, 109, 100, 243, 190

[56] References Cited

U.S. PATENT DOCUMENTS

| 3,353,756 | 11/1967 | Morgenson | 241/99 |
| 3,958,765 | 5/1976 | Musselman | 241/99 |
| 4,809,915 | 3/1989 | Koffsky et al. | 241/100 X |

FOREIGN PATENT DOCUMENTS

| 514335 | 8/1952 | Belgium | 241/199.12 |
| 937627 | 1/1956 | Fed. Rep. of Germany | 241/199.12 |
| 1146306 | 11/1957 | France | 241/199.12 |
| 19569 | 2/1979 | Japan | 241/100 X |

Primary Examiner—Mark Rosenbaum
Attorney, Agent, or Firm—Israel Nissenbaum

[57] ABSTRACT

A portable desk top "medical waste" fragmentation device and disposal system, complying with governmental requirements of maximum residual fragment size and sanitization. The fragmentation device includes a chamber having a rotating blade for fragmenting medical waste such as needles, syringes, vials and extracted teeth. For maximum effectiveness in reducing the medical waste into the requisite fragment size, the blade, with minimal clearance, passes between a U-shaped stationary member. During operation, the U-shaped member serves to momentarily hold the items to be fragmented in a stationary position as the blade fragments it in a shearing-type action. To ensure complete minimum size fragmentation, an agitating member continually throws the fragments into the path of the rotating blade. After the fragmentation is completed to the requisite size, the fragmentation chamber is opened into a disposal chute. The fragmented particles are drawn by centripetal force through the disposal chute into a removable and disposable receptacle having a sterilization or germicidal solution contained therein. The disposable receptacle, with sanitized waste, can thereafter be safely and legally thrown away as ordinary trash.

11 Claims, 4 Drawing Sheets

MEDICAL WASTE FRAGMENTATION AND DISPOSAL SYSTEM

This invention relates to devices for the disposal of medical wastes and more particularly to devices for the fragmentation and sanitization of medical wastes such as needles, syringes, vials and extracted teeth.

It is the general practice in the medical community for medical waste, such as used needles and syringes as well as testing vials, to be thrown into specially sealed red (to indicate hazardous waste) containers. The containers are periodically collected by a disposal service and dumped into huge disposal machines which pulverize and sterilize or incinerate the waste for further normal disposal such as in a landfill. Because of the gap in both time and distance between initial use and ultimate disposal, as well as the considerable expense involved, there is opportunity for abuse such as by illegal ocean dumping which has resulted in contamination of beach and fishing resources. To obviate such problems, various devices for the on-site destruction of used needles, syringes, vials and other medical wastes have been developed such as described in U.S. Pat. Nos. 3,683,733; 3,750,966; 3,785,233; 3,926,379; 3,929,295; 3,958,765; and 4,269,364. However, these devices are generally of a very complicated nature making their cost, for desk top use, prohibitively expensive. In addition, they are of varying degrees of effectiveness in fragmentation of particles to governmentally mandated size (i.e. capable of passing through a ⅛" sieve) and sanitization.

It is an object of the present invention to provide a relatively simple and economical, yet effective device for on-site fragmentation and sanitization of medical waste to minimum fragment size suitable for disposal in accordance with governmental standards.

It is a further object of the present invention to provide such fragmentation device with a sanitization and disposal system.

It is a still further object of the present invention to provide a fragmentation and sanitization disposal device and system requiring minimal manual handling.

These and other objects features and advantages of the present invention will become more evident from the following discussion and drawings in which.

Figure 1:
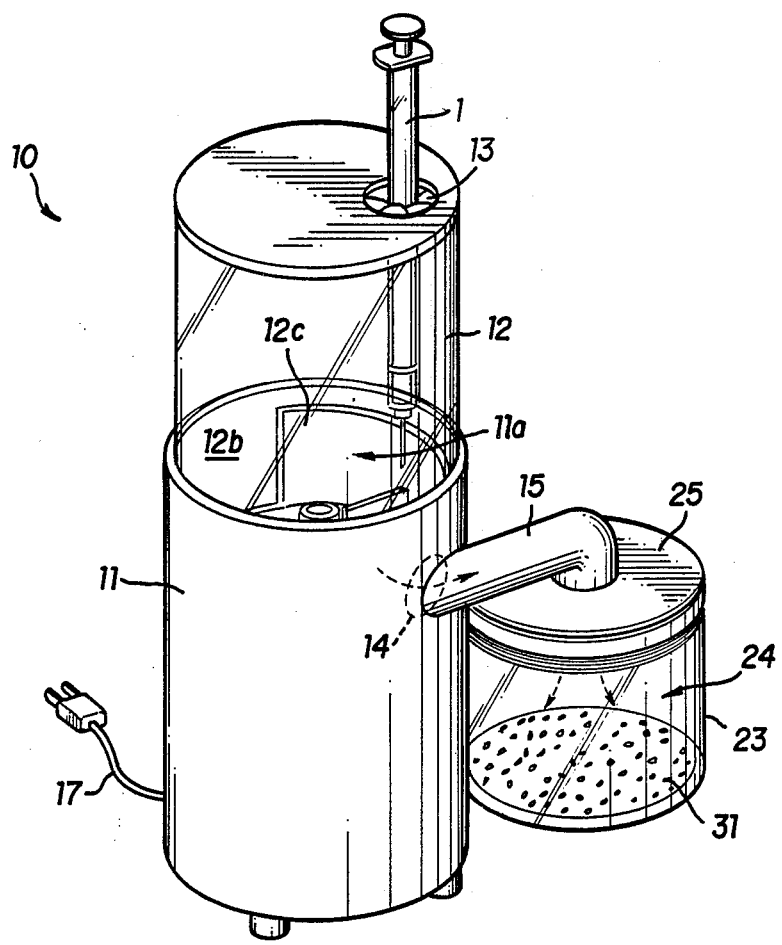
FIG. 1 is an isometric view of the fragmentation device and sanitization system of the present invention.

Generally the present invention comprises a portable desk top "medical waste" fragmentation device and disposal system complying with governmental requirements of maximum residual fragment size (capable of passing through a ⅛" sieve) and sanitization. The fragmentation device comprises a container such as a cylinder with a diameter typically between about 3 to 6 inches (7.6–15.4 cm). The container has a self contained motor, and a separate fragmentation chamber containing a horizontal rotating blade, powered by the motor. A rotational speed in excess of 1600 rpm for the blade is desirable for efficient shearing and fragmentation by the blade. In addition, to prevent jamming during operation, it is preferred that the motor exert a relatively high torque with a rating of least ¼ horsepower.

The fragmentation chamber is provided with two openings. The first opening, of relatively larger size, is closed off with a cover member having an aperture therein which permits direct introduction of the medical waste into the fragmentation chamber. The cover is, however, removable for servicing. The second, smaller opening, leads to a disposal chute for evacuation of the fragmented particles of medical waste into a disposable sanitization receptacle. The cover member is provided with a one way port such as a spring loaded member to prevent accidental expulsion of any particles.

In a second embodiment, more suitable for smaller waste such as extracted teeth, a small holding chamber may be provided for holding the medical waste until a sufficient amount has been accumulated for fragmentation. In such embodiment, waste introduction means permits selective dumping of the medical waste into the fragmentation chamber through the first opening after the fragmentation blade has been activated. To prevent injury, a safety cut-off switch prevents the fragmentation blade from rotating if the cover or holding chamber is removed. In a simple, preferred embodiment, the holding chamber is a second receptacle fitted within the cover member and the cover member is rotatable relative thereto. The cover has a semi-circular section which functions as the base of the holding chamber. When the cover is rotated, the semi-circular section is removed from the holding chamber and the contents thereof fall into the fragmentation chamber below.

For maximum effectiveness in reducing the medical waste into the requisite fragment size, means for temporarily holding the medical waste for fragmentation by the blade is utilized. Preferably such means comprises one or more rigid stationary members fixedly attached to the wall of the fragmentation chamber and extending in a direction parallel to the plane of the moving blade. The stationary members are spaced from the plane by a distance no greater than about 0.25 inch (0.64 cm) to insure fragmentation below the governmental limits. In addition, the stationary members extend for a distance at least half the radius of the circle circumscribed by the rotating blade. In a preferred embodiment, the blade, with minimal clearance, passes between the elements of a U-shaped stationary member which extends inwardly from the wall of the fragmentation chamber over a substantial portion of the rotating blade. During operation, the U-shaped member serves as a means to momentarily hold the needle, syringe or vial (and fragments thereof) in a stationary position as the blade fragments it in a shearing-type action. Examples of such U-shaped member include two closely spaced metal rods embedded in the wall of the fragmentation chamber or a one piece unit having a base which is attached to or imbedded in the wall of the fragmentation chamber.

To ensure complete minimum size fragmentation, an agitating member continually throws the fragments into the path of the rotating blade. Such agitating member is preferably a radially extending metal sweeper blade with airfoil or radially extending wire which rotates about the same axis as the fragmentation blade but in a plane in close juxtaposition to the base of the fragmentation chamber where the fragments tend to settle. Depending upon the speed of the rotating blade it may be aligned or offset from the fragmentation blade to provide optimal fragment throw into the blade path as it passes between the stationary U-shaped member.

After the fragmentation is completed to the requisite size (generally after about 15 seconds), means are deployed for opening the fragmentation chamber into a disposal chute. It is undesirable for the fragmentation chamber to be constantly opened into the disposal chute since particles of excessive size may be prematurely drawn therethrough. With continued blade rotation, the fragmented particles are drawn by centripetal force through the disposal chute into a removable disposable receptacle having a sanitization solution contained therein. The disposable receptacle can thereafter be safely and legally thrown away as ordinary trash. For simplicity it is preferred that rotation of the cover member causes the opening to the disposal chute to be selectively opened and closed. The U-shaped member serves as a stop for such rotation for both the open and closed positions.

In the embodiment having a holding chamber, the cover with the holding chamber is movable relative to the first opening in the fragmentation chamber whereby such movement permits the selective dumping of the medical waste into the fragmentation chamber. At the same time such movement closes the second opening leading to the disposal chute whereby the medical waste is continuously fragmented prior to any evacuation. Movement of the cover member to its original position closes the first opening and opens the second disposal opening whereby more waste may be loaded into the holding chamber and at the same time the fragmented waste is evacuated into the disposal chute. The stationary U-shaped member serves as a stop for the movement of the cover member in such embodiment for the opening and closing of both the first and second openings. In another embodiment, for use if the motor and fragmentation chamber are relatively large, the medical waste is continuously directly introduced into the fragmentation chamber and periodically evacuated as needed.

As part of the disposal system, the disposal chute terminates in a member which sealingly engages, such as by a screw thread or bayonet mount, a disposable waste receptacle containing a sterilization or germicidal solution, such as ammonia or chlorine. The solution need only be germicidal in nature in order to render the fragmented particles safe and it may simply be a strong disinfectant. It need not provide complete sterilization. When the fragmented particles have been sanitized to such degree, the sealing member is disengaged from the receptacle (for re-use in sealing a fresh receptacle) and the receptacle is otherwise closed and disposed of as ordinary trash. During the entire operation of the device until ultimate disposal, the only manual handling and exposure of the medical waste occurs at the initial introduction of such waste into the device.

Figure 2:
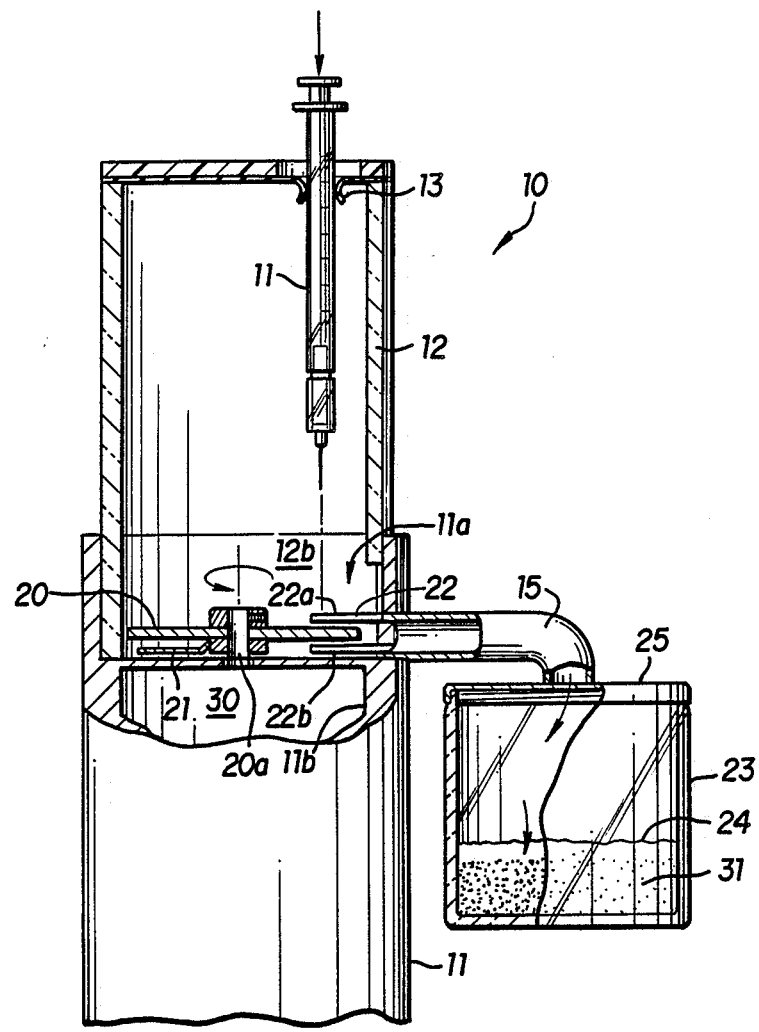
FIG. 2 is a partial sectioned side view of the device of FIG. 1.
Figure 3:
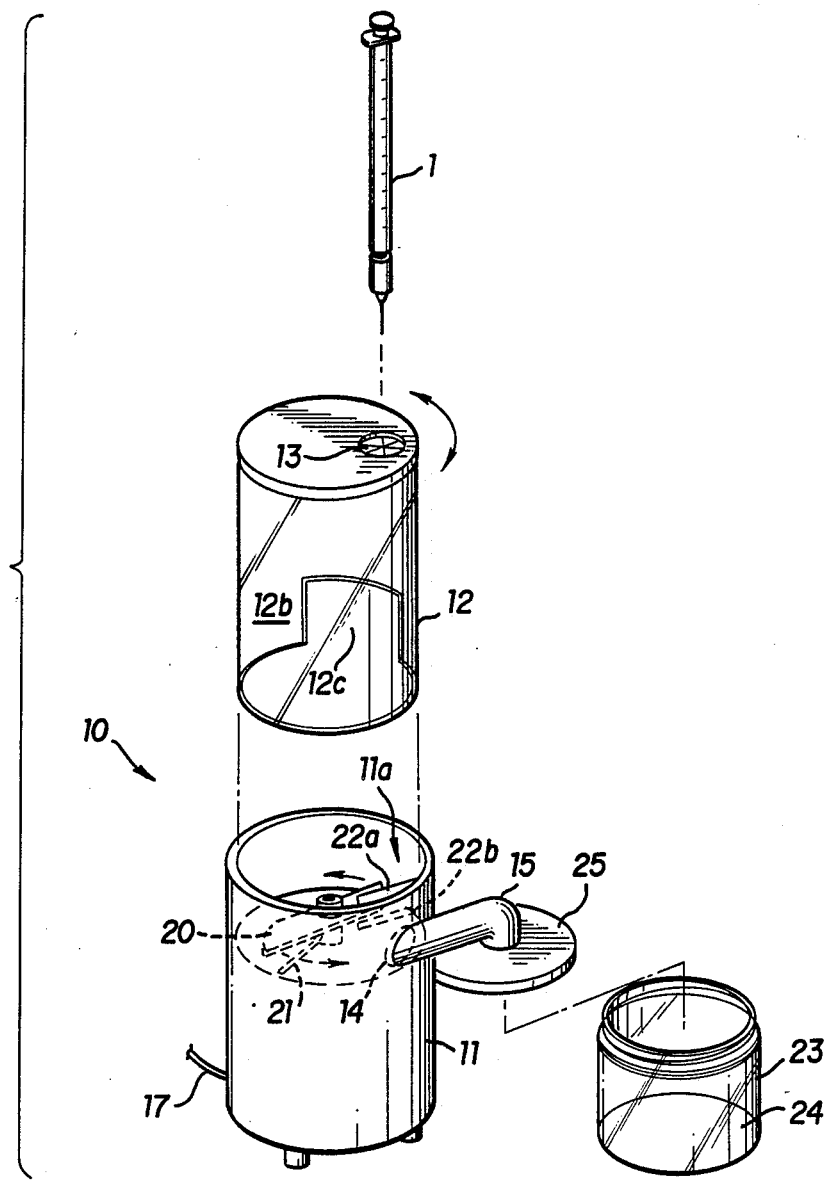
FIG. 3 is an exploded view of the major component elements of the device of FIG. 1.

With specific reference to the drawings, as seen in FIGS. 1-3, fragmentation and sanitization device 10 is comprised of a cylindrical body 11 made of a molded hard plastic or metal material. The cylindrical body 11 has enclosed chamber 11b for containment of an electric motor 30 which is powered by an external electrical source via electric cord 17. Open ended fragmentation chamber 11a contains metallic blade 20 mounted on rotating shaft 20a which is driven by electric motor 30.

To minimize jamming and to ensure small particle size formation, the electric motor provides sufficient power to rotate the blade at speeds in excess of 1600 rpm with a high torque and rating of at least ¼ horsepower. The open or exposed end of fragmentation chamber 11a is closed by open ended cylindrical cover member 12 which is adapted to snugly, though rotatably, fit within the inner walls of the fragmentation chamber 11a.

Figure 4:
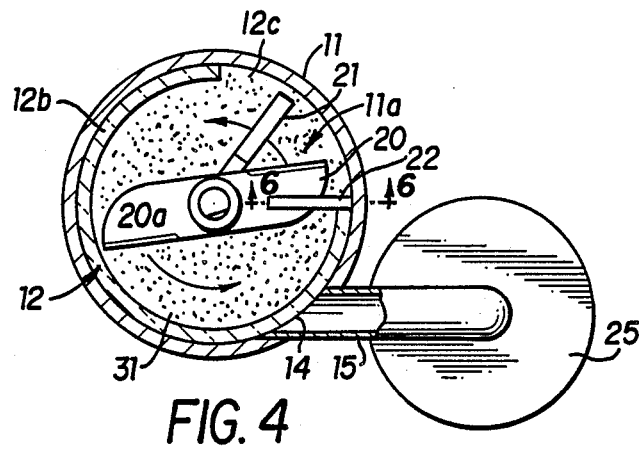
FIG. 4 is a partial sectioned plan view of the fragmentation chamber during fragmentation.
Figure 5:
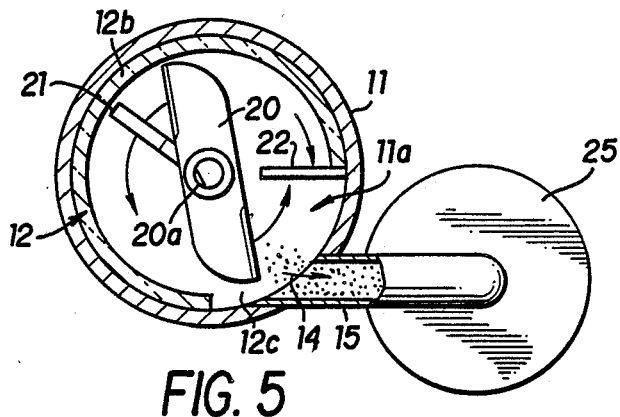
FIG. 5 is a partial sectioned plan view of the fragmentation chamber after completion of fragmentation and evacuation of the particles through the disposal chute.
Figure 6:
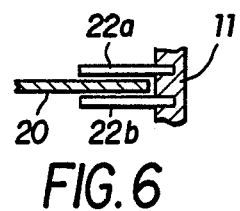
FIG. 6 is a sectioned view taken along line 6—6 of FIG. 4 showing the shearing action of the fragmentation blade.

As is more clearly evident from FIGS. 4 and 5, metal blade 20 is a straight elongated flat piece of metal with a central aperture for engagement with the rotating shaft 20a. The blade 20 has rounded ends to minimize jamming and is sized to be slightly distanced from the inner walls of the base of the cover member 12 which is interfit within the walls of the fragmentation chamber 11a. A substantial portion of the straight blade 20 passes through U-shaped metal member 22 which is laterally imbedded in the walls of the fragmentation chamber 11a. As seen in FIG. 6, there is minimal clearance between the blade 20 and the U-shaped member 22 to facilitate shearing of the medical waste to minimal size. To further facilitate shearing action of the medical waste, the blade is sharpened on its leading edges which enter between the elements of the U-shaped member 22 on its rotational path.

During operation, medical waste such as used needle and syringe 1 is inserted through one-way opening 13 in cover member 12. As shown in FIG. 4, lower flange 12b of cover member 12 is rotated into position to close off access from the fragmentation chamber 11a to opening 14 which leads to disposal chute 15. The cutout 12c of the cover member 12 (shown most clearly in FIG. 3) is specifically sized in cooperation with U-shaped member 22 as a stop, to permit rotation of the cover member 12 for opening and closing of the disposal chute opening 14 (FIGS. 4–5).

To prevent possible jamming, the motor is electrically activated before the medical waste has been loaded into the fragmentation chamber 11a. The blade 20 rapidly rotates and fragments the waste into progressively smaller particles. Closure of the opening 14 by cover member flange 12b ensures that no excessively sized fragment is evacuated prior to complete fragmentation. To ensure such complete fragmentation, i.e. to a size which passes through a ½" sieve, as governmentally mandated, U-shaped member 22 acts to momentarily hold the fragments as the blade 20 shears them while passing between the extension elements 22a and 22b of the U-shaped member. Fragments which fall to the base of the fragmentation chamber are agitated into the blade path by sweeper blade agitation member 21 which is rotated by motor shaft 20a and located adjacent the base of the fragmentation chamber 11a.

When fragmentation is complete, the cover member is rotated as shown in FIG. 5 to a position whereby opening 14 is made accessible to the fragmented particles 30 in the fragmentation chamber. These particles are caused, by continual centripetal force exerted by the still rotating blade 20, to be swept through both opening 14 and then disposal chute 15 into jar 23 which also contains sterilizing solution 24. Jar 23 is removably attached to cover member 25 which is in turn affixed to the lower end of the disposal chute 15. After the fragmented particles are loaded into the jar 23 with sanitization material, the jar is removed from cover member 25, typically by unscrewing, and is covered by other means such as by another screw-on cover. The jar, with sanitized and fragmented medical waste is disposed of as ordinary trash.

It is understood that the above detailed description of the present invention is presented for illustrative purposes and that changes may be made in construction, configuration and materials of the components of the present invention such as by the inclusion of additional blade elements and the like, without departing from the scope of the present invention as defined in the following claims.

What is claimed is:

1. A device for the fragmentation, sanitization and disposal of medical waste; the device comprising a container having a motor enclosed therewithin and a fragmentation chamber, separated from the motor, said device further comprising a disposal chute, opening into the fragmentation chamber, for evacuation of fragmented particles of medical waste into a disposable receptacle containing means for sanitizing the fragmented particles, said disposal chute having means for sealing engagement and disengagement with the disposable receptacle; with the fragmentation chamber containing a rotating blade, powered by the motor; said fragmentation chamber having two openings, a first opening for introduction of medical waste into the fragmentation chamber, for fragmentation by the rotating blade; and a second opening which leads to the disposal chute, said device further having means for selectively opening and closing the second opening, with said second opening being selectively opened while the blade is rotating, to effect said evacuation.

2. The device of claim 1 wherein said motor has a rating of at least ¼ horsepower and rotates the blade at a speed of at least 1600 rpm.

3. The device of claim 1 wherein the fragmentation chamber further includes means for temporarily holding the medical waste for shearing fragmentation by the rotating blade.

4. The device of claim 3 wherein the means for temporarily holding the medical waste comprises one or more rigid stationary members fixedly attached to the wall of the fragmentation chamber and extending in a direction parallel to the plane of the moving blade, with said stationary members being spaced from said plane by a distance no greater than 0.25 inch (0.64 cm) and wherein the stationary members extend for a distance at least half the radius of the circle circumscribed by the rotating blade.

5. The device of claim 4 wherein said rigid stationary members comprise a U-shaped member having parallel elements between which the rotating blade passes.

6. The device of claim 5 wherein said rotating blade comprises an elongated flat metal member having rounded ends and having sharpened sections on the leading edges thereof which pass between the parallel elements of said U-shaped member during the rotation of the blade.

7. The device of claim 4 wherein the device further includes an agitating member which rotates in concert with the rotating blade in a plane substantially parallel to the plane of the rotating blade, said agitating member rotating in a plane adjacent the base of the fragmentation chamber.

8. The device of claim 7 wherein said agitating member comprises a radially extending sweeper blade with airfoil.

9. The device of claim 7 wherein said agitating member comprises a radially extending wire.

10. A device for the fragmentation, sanitization and disposal of medical waste; the device comprising a container having a motor enclosed therewithin and a fragmentation chamber, separated from the motor, said device further comprising a disposal chute, opening into the fragmentation chamber, for evacuation of fragmented particles of medical waste into a disposable receptacle containing means for sanitizing the fragmented particles, said disposal chute having means for sealing engagement and disengagement with the disposable receptacle; with the fragmentation chamber containing a rotating blade, powered by the motor; said fragmentation chamber having two openings, a first opening for introduction of medical waste into the fragmentation chamber, for fragmentation by the rotating blade; and a second opening which leads to the disposal chute, said device further having means for selectively opening and closing the second opening, with said second opening being selectively opened while the blade is rotating, to effect said evacuation; wherein said first opening is closed by a cover member having a portion thereof which is interfitted within the walls of said fragmentation chamber and is rotatable relative to said fragmentation chamber whereby said portion of the cover member selectively opens and closes said second opening.

11. The device of claim 10 wherein said cover member comprises a one way opening therein for introduction of medical waste into the fragmentation chamber.

* * * * *